US008188127B2

(12) United States Patent
Levy et al.

(10) Patent No.: US 8,188,127 B2
(45) Date of Patent: May 29, 2012

(54) MICROBICIDAL COMPOSITION

(75) Inventors: Richard Levy, Valbonne (FR); Beverly Jean El A'mma, Perkiomenville, PA (US); Beat Heer, Grabs (CH); Kiran Pareek, Bensalem, PA (US)

(73) Assignee: Rohm and Haas Company, Philadelphia, PA (US)

( * ) Notice: Subject to any disclaimer, the term of this patent is extended or adjusted under 35 U.S.C. 154(b) by 610 days.

(21) Appl. No.: 12/217,680

(22) Filed: Jul. 8, 2008

(65) Prior Publication Data
US 2009/0023688 A1  Jan. 22, 2009

(30) Foreign Application Priority Data

Jul. 18, 2007  (EP) .................................... 07290901

(51) Int. Cl.
*A01N 43/80* (2006.01)
*A01N 43/76* (2006.01)
*A01N 57/10* (2006.01)
*A01N 43/66* (2006.01)
*A01N 43/78* (2006.01)
*A01N 37/02* (2006.01)
*A01N 37/00* (2006.01)
*A01N 37/12* (2006.01)
*A01N 31/00* (2006.01)

(52) U.S. Cl. ........ 514/373; 514/143; 514/241; 514/367; 514/374; 514/552; 514/558; 514/561; 514/738

(58) Field of Classification Search ................... 514/143, 514/373, 241, 374, 558, 738, 552, 367, 561
See application file for complete search history.

(56) References Cited

U.S. PATENT DOCUMENTS

| 2,466,663 | A | | 4/1949 | Russ et al. |
| 4,337,269 | A | | 6/1982 | Berke et al. |
| 4,725,612 | A | | 2/1988 | Mahn et al. |
| 5,516,510 | A | | 5/1996 | Beilfuss et al. |
| 5,633,278 | A | | 5/1997 | Oppong et al. |
| 5,648,348 | A | | 7/1997 | Fost et al. |
| 5,736,574 | A | * | 4/1998 | Burnier et al. ............ 514/563 |
| 6,241,994 | B1 | * | 6/2001 | Lee et al. .................. 424/408 |
| 6,432,433 | B1 | | 8/2002 | Winkowski et al. |
| 2004/0198785 | A1 | | 10/2004 | Heer et al. |
| 2006/0135384 | A1 | | 6/2006 | Luu et al. |
| 2007/0078118 | A1 | * | 4/2007 | Levy et al. ................. 514/373 |
| 2010/0305211 | A1 | | 12/2010 | Modak et al. |

FOREIGN PATENT DOCUMENTS

| EP | 0236119 | | 9/1987 |
| EP | 0488606 | | 6/1996 |
| EP | 1665933 | | 6/2006 |
| GB | 2274779 A | | 8/1994 |
| GB | 2326167 | | 12/1998 |
| JP | 10298012 A | | 11/1998 |
| JP | 11012109 A | | 1/1999 |
| JP | 2001302418 A | * | 10/2001 |
| WO | WO2007007080 | | 1/2007 |
| WO | WO2007026004 | | 3/2007 |
| WO | 2007098135 | | 8/2007 |

OTHER PUBLICATIONS

Rossmoore et al., Factors Affecting Selection of Metalworking Fluid Biocides, Tribos 94, 1994, pp. 1-11.*
English translation of JP 2001302418 A filed Oct. 2001.*
Morley, et al., "Structure-activity relationships in 3-Isothiazolones", Org. Biomol. Chem., vol. 3, pp. 3713-3719 (2005).
"Bioban CS-1246" Dow, USA, http://www.dow.com/PublishedLiterature . . . , p. 2, (2002).
"Applications of Biomimetic phospholipids in 'preservative-free' formulations," Chemical Abstracts Services, Columbus, Ohio, pp. 515-515 (2005).
Marounek, et. al., "Susceptibility of *Escherichia coli* to C2-C18 fatty acids," vol. 48, No. 6, pp. 731-735 (2003).

* cited by examiner

*Primary Examiner* — Kevin E Weddington
(74) *Attorney, Agent, or Firm* — Kenneth Crimaldi

(57) ABSTRACT

Synergistic microbicidal compositions containing N-methyl-1,2-benzisothiazolin-3-one.

11 Claims, No Drawings

MICROBICIDAL COMPOSITION

This patent application claims the benefit of the earlier filed European Patent application serial number 07290901.3 filed on Jul. 18, 2007 under 37 CFR 1.55(a).

This invention relates to a synergistic combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, U.S. Pat. App. Pub. No. 2007/0078118 discloses synergistic combinations of N-methyl-1,2-benzisothiazolin-3-one (MBIT) with other biocides. However, there is a need for additional combinations of microbicides having enhanced activity against various strains of microorganisms to provide effective control of the microorganisms. Moreover, there is a need for combinations containing lower levels of individual microbicides for environmental and economic benefit. The problem addressed by this invention is to provide such additional combinations of microbicides.

STATEMENT OF THE INVENTION

The present invention is directed to a microbicidal composition comprising: (a) N-methyl-1,2-benzisothiazolin-3-one; and (b) at least one microbicide selected from the group consisting of hexahydro-1,3,5-tris(2-hydroxyethyl)-s-triazine; 4,4-dimethyloxazolidine; sodium hydroxymethylglycinate; myristamidopropyl PG-dimoonium chloride phosphate; octanoic acid; 2-ethylhexyl glycerin; glyceryl monocaprylate; glyceryl monocaprate; 7α-ethyldihydro-1H, 3H,5H-oxazolo (3,4-C) oxazole; and 2-(thiocyanomethylthio)benzothiazole.

DETAILED DESCRIPTION OF THE INVENTION

As used herein, the following terms have the designated definitions, unless the context clearly indicates otherwise. "MBIT" is N-methyl-1,2-benzisothiazolin-3-one. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w).

The compositions of the present invention unexpectedly have been found to provide enhanced microbicidal efficacy at a combined active ingredient level lower than that of the individual microbicides. Additional microbicides beyond those listed in the claims may be present in the composition.

In one embodiment of the invention, the antimicrobial composition comprises N-methyl-1,2-benzisothiazolin-3-one and hexahydro-1,3,5-tris(2-hydroxyethyl)-s-triazine. Preferably, a weight ratio of hexahydro-1,3,5-tris(2-hydroxyethyl)-s-triazine to N-methyl-1,2-benzisothiazolin-3-one is from 1:0.0014 to 1:150, more preferably from 1:0.012 to 1:150.

In one embodiment of the invention, the antimicrobial composition comprises N-methyl-1,2-benzisothiazolin-3-one and 4,4-dimethyloxazolidine. Preferably, a weight ratio of 4,4-dimethyloxazolidine to N-methyl-1,2-benzisothiazolin-3-one is from 1:0.0011 to 1:3.5.

In one embodiment of the invention, the antimicrobial composition comprises N-methyl-1,2-benzisothiazolin-3-one and sodium hydroxymethylglycinate. Preferably, a weight ratio of sodium hydroxymethylglycinate to N-methyl-1,2-benzisothiazolin-3-one is from 1:0.0005 to 1:2.3, more preferably from 1:0.14 to 1:2.3, more preferably from 1:0.29 to 1:2.3.

In one embodiment of the invention, the antimicrobial composition comprises N-methyl-1,2-benzisothiazolin-3-one and myristamidopropyl PG-dimoonium chloride phosphate. Preferably, a weight ratio of myristamidopropyl PG-dimoonium chloride phosphate to N-methyl-1,2-benzisothiazolin-3-one is from 1:0.0011 to 1:150.

In one embodiment of the invention, the antimicrobial composition comprises N-methyl-1,2-benzisothiazolin-3-one and octanoic acid. Preferably, a weight ratio of octanoic acid to N-methyl-1,2-benzisothiazolin-3-one is from 1:0.0046 to 1:0.68, more preferably from 1:0.029 to 1:0.68.

In one embodiment of the invention, the antimicrobial composition comprises N-methyl-1,2-benzisothiazolin-3-one and 2-ethylhexyl glycerin. Preferably, a weight ratio of 2-ethylhexyl glycerin to N-methyl-1,2-benzisothiazolin-3-one is from 1:0.017 to 1:2.3.

In one embodiment of the invention, the antimicrobial composition comprises N-methyl-1,2-benzisothiazolin-3-one and glyceryl monocaprylate. Preferably, a weight ratio of glyceryl monocaprylate to N-methyl-1,2-benzisothiazolin-3-one is from 1:0.0004 to 1:75, more preferably from 1:0.012 to 1:75.

In one embodiment of the invention, the antimicrobial composition comprises N-methyl-1,2-benzisothiazolin-3-one and glyceryl monocaprate. Preferably, a weight ratio of glyceryl monocaprate to N-methyl-1,2-benzisothiazolin-3-one is from 1:0.0031 to 1:8.8, more preferably from 1:0.017 to 1:8.8.

In one embodiment of the invention, the antimicrobial composition comprises N-methyl-1,2-benzisothiazolin-3-one and 7α-ethyldihydro-1H,3H,5H-oxazolo (3,4-C) oxazole. Preferably, a weight ratio of 7α-ethyldihydro-1H, 3H,5H-oxazolo (3,4-C) oxazole to N-methyl-1,2-benzisothiazolin-3-one is from 1:0.0003 to 1:7.1.

In one embodiment of the invention, the antimicrobial composition comprises N-methyl-1,2-benzisothiazolin-3-one and 2-(thiocyanomethylthio)benzothiazole. Preferably, a weight ratio of 2-(thiocyanomethylthio)benzothiazole to N-methyl-1,2-benzisothiazolin-3-one is from 1:0.063 to 1:143.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms or higher forms of aquatic life (such as protozoans, invertebrates, bryozoans, dinoflagellates, crustaceans, mollusks, etc.) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners and sanitary wipes; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives, such as ceramic adhesives, carpet backing adhesives, photographic chemicals, printing fluids, household products such as bathroom and kitchen cleaners and sanitary wipes, cosmetics, toiletries, shampoos, soaps, detergents, industrial cleaners, floor polishes, laundry rinse water, metal working fluids, textile products, wood and wood products, agriculture adjuvant preservation, surfactant preservation, diagnostic reagent preservation, food preservation, and food, beverage, and industrial process pasteurizers.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, more preferably at least 4 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index (``SI'')}$$

wherein:
 $Q_A$=concentration of compound A (first component) in ppm, acting alone, which produced an end point (MIC of Compound A).
 $Q_a$=concentration of compound A in ppm, in the mixture, which produced an end point.
 $Q_B$=concentration of compound B (second component) in ppm, acting alone, which produced an end point (MIC of Compound B).
 $Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides was tested by conducting high resolution MIC assays in the presence of various concentrations of MBIT. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient.

The synergy of the combinations of the present invention was determined against several microorganisms, as described in the Tables below. The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the MBIT combinations of the present invention are shown below in Tables 1 through 10. In each test, Second Component (B) was MBIT and the First Component (A) was the other commercial microbicide. Each table shows the specific combinations of MBIT and the other component; results against the microorganisms tested with incubation times; the end-point activity in ppm measured by the MIC for MBIT alone ($Q_B$), for the other component alone ($Q_A$), for MBIT in the mixture ($Q_b$) and for the other component in the mixture ($Q_a$); the calculated SI value; and the range of synergistic ratios for each combination tested (other component/MBIT or A/B).

TABLE 1

| Test Organisms | Contact Time | Ca | Cb | S.I. | Ca:Cb |
| --- | --- | --- | --- | --- | --- |
| A. niger ATCC # 16404 | 3 days | 425 | — | — | — |
| | | — | 37.5 | — | — |
| | | 110 | 18.8 | 0.76 | 1:0.1709 |
| | | 200 | 18.8 | 0.97 | 1:0.0940 |
| | | 300 | 18.8 | 1.21 | 1:0.0627 |
| | | 300 | 9.4 | 0.96 | 1:0.0313 |
| | | 425 | 9.4 | 1.25 | 1:0.0221 |
| | | 300 | 4.7 | 0.83 | 1:0.0157 |
| | | 425 | 4.7 | 1.13 | 1:0.0111 |
| | | 300 | 2.4 | 0.77 | 1:0.0080 |
| | | 425 | 2.4 | 1.06 | 1:0.0056 |
| | | 300 | 1.2 | 0.74 | 1:0.0040 |
| | | 425 | 1.2 | 1.03 | 1:0.0028 |
| | 7 days | 650 | — | — | — |
| | | — | 150 | — | — |
| | | 42.5 | 75 | 0.57 | 1:1.7647 |
| | | 65 | 75 | 0.60 | 1:1.1538 |
| | | 110 | 75 | 0.67 | 1:0.6818 |
| | | 200 | 75 | 0.81 | 1:0.3750 |
| | | 300 | 75 | 0.96 | 1:0.2500 |
| | | 400 | 75 | 1.12 | 1:0.1875 |
| | | 425 | 18.8 | 0.78 | 1:0.0442 |
| | | 525 | 18.8 | 0.93 | 1:0.0358 |
| | | 650 | 9.4 | 1.06 | 1:0.0145 |

TABLE 1-continued

| Test Organisms | Contact Time | Ca | Cb | S.I. | Ca:Cb |
| --- | --- | --- | --- | --- | --- |
| | | 525 | 4.7 | 0.84 | 1:0.0090 |
| | | 650 | 4.7 | 1.03 | 1:0.0072 |
| | | 525 | 2.4 | 0.82 | 1:0.0046 |
| | | 650 | 2.4 | 1.02 | 1:0.0037 |
| | | 650 | 1.2 | 1.01 | 1:0.0018 |
| C. albicans ATCC # 10231 | 48 hrs | 875 | — | — | — |
| | | — | 30 | — | — |
| | | 87.5 | 15 | 0.60 | 1:0.1714 |
| | | 110 | 15 | 0.63 | 1:0.1364 |
| | | 200 | 15 | 0.73 | 1:0.0750 |
| | | 300 | 15 | 0.84 | 1:0.0500 |
| | | 425 | 15 | 0.99 | 1:0.0353 |
| | | 110 | 7.5 | 0.38 | 1:0.0682 |
| | | 200 | 7.5 | 0.48 | 1:0.0375 |
| | | 300 | 7.5 | 0.59 | 1:0.0250 |
| | | 425 | 7.5 | 0.74 | 1:0.0176 |
| | | 525 | 7.5 | 0.85 | 1:0.0143 |
| | | 650 | 7.5 | 0.99 | 1:0.0115 |
| | | 425 | 3.75 | 0.61 | 1:0.0088 |
| | | 525 | 3.75 | 0.73 | 1:0.0071 |
| | | 650 | 3.75 | 0.87 | 1:0.0058 |
| | | 875 | 3.75 | 1.13 | 1:0.0043 |
| | | 650 | 1.86 | 0.80 | 1:0.0029 |
| | | 875 | 1.86 | 1.06 | 1:0.0021 |
| | | 650 | 0.94 | 0.77 | 1:0.0014 |
| | | 875 | 0.94 | 1.03 | 1:0.0011 |
| | 72 hrs | 875 | — | — | — |
| | | — | 30 | — | — |
| | | 87.5 | 15 | 0.60 | 1:0.1714 |
| | | 110 | 15 | 0.63 | 1:0.1364 |
| | | 200 | 15 | 0.73 | 1:0.0750 |
| | | 300 | 15 | 0.84 | 1:0.0500 |
| | | 425 | 15 | 0.99 | 1:0.0353 |
| | | 425 | 7.5 | 0.74 | 1.0.0176 |
| | | 525 | 7.5 | 0.85 | 1:0.0143 |
| | | 650 | 7.5 | 0.99 | 1:0.0115 |
| | | 875 | 1.86 | 1.06 | 1:0.0021 |
| | | 875 | 0.94 | 1.03 | 1:0.0011 |
| Ps. aeruginosa ATCC # 9027 | 24 hrs | 55 | — | — | — |
| | | — | 75 | — | — |
| | | 32.5 | 37.5 | 1.09 | 1:1.1538 |
| | | 43.75 | 18.75 | 1.05 | 1:0.4286 |
| | | 43.75 | 9.4 | 0.92 | 1:0.2149 |
| | | 43.75 | 4.6 | 0.86 | 1:0.1051 |
| | 48 hrs | 55 | — | — | — |
| | | — | 125 | — | — |
| | | 26.25 | 75 | 1.08 | 1:2.8571 |
| | | 32.5 | 37.5 | 0.89 | 1:1.1538 |
| | | 43.75 | 37.5 | 1.10 | 1:0.8571 |
| | | 55 | 4.6 | 1.04 | 1:0.0836 |
| S. aureus ATCC # 6538 | 24 hrs | 55 | — | — | — |
| | | — | 15 | — | — |
| | | 15 | 7.5 | 0.77 | 1:0.5000 |
| | | 32.5 | 3.8 | 0.84 | 1:0.1169 |
| | | 43.75 | 3.8 | 1.05 | 1:0.0869 |
| | | 32.5 | 1.8 | 0.71 | 1:0.0554 |
| | | 43.75 | 1.8 | 0.92 | 1:0.0411 |
| | | 55 | 1.8 | 1.12 | 1:0.0327 |
| | | 55 | 0.94 | 1.06 | 1:0.0171 |
| | 48 hrs | 55 | — | — | — |
| | | — | 30 | — | — |
| | | 0.1 | 15 | 0.50 | 1:150.0000 |
| | | 1.5 | 15 | 0.53 | 1:10.0000 |
| | | 2.625 | 15 | 0.55 | 1:5.7143 |
| | | 4.375 | 15 | 0.58 | 1:3.4286 |
| | | 5.5 | 15 | 0.60 | 1:2.7273 |
| | | 10 | 15 | 0.68 | 1:1.5000 |
| | | 15 | 15 | 0.77 | 1:1.0000 |
| | | 21.25 | 15 | 0.89 | 1:0.7059 |
| | | 26.25 | 15 | 0.98 | 1:0.5714 |
| | | 32.5 | 15 | 1.09 | 1:0.4615 |
| | | 21.25 | 7.5 | 0.64 | 1:0.3529 |
| | | 26.25 | 7.5 | 0.73 | 1:0.2857 |
| | | 32.5 | 7.5 | 0.84 | 1:0.2308 |
| | | 43.75 | 7.5 | 1.05 | 1:0.1714 |
| | | 32.5 | 3.8 | 0.72 | 1:0.1169 |
| | | 43.75 | 3.8 | 0.92 | 1:0.0869 |

TABLE 1-continued

| Test Organisms | Contact Time | Ca | Cb | S.I. | Ca:Cb |
|---|---|---|---|---|---|
| | | 55 | 3.8 | 1.13 | 1:0.0691 |
| | | 32.5 | 1.8 | 0.65 | 1:0.0554 |
| | | 55 | 1.8 | 1.06 | 1:0.0327 |
| | | 43.75 | 0.94 | 0.83 | 1:0.0215 |
| | | 55 | 0.94 | 1.03 | 1:0.0171 |

Ca: ppm AI of BIOBAN GK(hexahydro-1,3,5-tris(2-hydroxyethyl)-s-triazine)
Cb: ppm AI of MBIT(N-methyl-1,2-benzisothiazolin-3-one)
Ratio: Ca:Cb

TABLE 2

| Test Organisms | Contact Time | Ca | Cb | S.I. | Ca:Cb |
|---|---|---|---|---|---|
| A. niger ATCC # 16404 | 3 days | 525 | — | — | — |
| | | — | 37.5 | — | — |
| | | 200 | 18.8 | 0.88 | 1:0.0940 |
| | | 300 | 18.8 | 1.07 | 1:0.0627 |
| | | 300 | 9.4 | 0.82 | 1:0.0313 |
| | | 425 | 9.4 | 1.06 | 1:0.0221 |
| | | 425 | 4.7 | 0.93 | 1:0.0111 |
| | | 525 | 4.7 | 1.13 | 1:0.0090 |
| | | 425 | 2.4 | 0.87 | 1:0.0056 |
| | | 525 | 2.4 | 1.06 | 1:0.0046 |
| | | 425 | 1.2 | 0.84 | 1:0.0028 |
| | | 525 | 1.2 | 1.03 | 1:0.0023 |
| | 7 days | 875 | — | — | — |
| | | — | 150 | — | — |
| | | 525 | 75 | 1.1 | 1:0.1429 |
| | | 650 | 37.5 | 0.99 | 1:0.0577 |
| | | 875 | 9.4 | 1.06 | 1:0.0107 |
| | | 650 | 4.7 | 0.77 | 1:0.0072 |
| | | 875 | 4.7 | 1.03 | 1:0.0054 |
| | | 650 | 2.4 | 0.76 | 1:0.0037 |
| | | 875 | 2.4 | 1.02 | 1:0.0027 |
| | | 875 | 1.2 | 1.01 | 1:0.0014 |
| C. albicans ATCC # 10231 | 48 hrs | 1100 | — | — | — |
| | | — | 30 | — | — |
| | | 425 | 15 | 0.89 | 1:0.0353 |
| | | 525 | 15 | 0.98 | 1:0.0286 |
| | | 650 | 15 | 1.09 | 1:0.0231 |
| | | 650 | 7.5 | 0.84 | 1:0.0115 |
| | | 875 | 7.5 | 1.05 | 1:0.0086 |
| | | 875 | 3.75 | 0.92 | 1:0.0043 |
| | | 1100 | 3.75 | 1.13 | 1:0.0034 |
| | | 875 | 1.86 | 0.86 | 1:0.0021 |
| | | 1100 | 1.86 | 1.06 | 1:0.0017 |
| | | 875 | 0.94 | 0.83 | 1:0.0011 |
| | | 1100 | 0.94 | 1.03 | 1:0.0009 |
| | 72 hrs | 1100 | — | — | — |
| | | — | 30 | — | — |
| | | 425 | 15 | 0.89 | 1:0.0353 |
| | | 525 | 15 | 0.98 | 1:0.0286 |
| | | 650 | 15 | 1.09 | 1:0.0231 |
| | | 875 | 7.5 | 1.05 | 1:0.0086 |
| | | 875 | 3.75 | 0.92 | 1:0.0043 |
| | | 1100 | 3.75 | 1.13 | 1:0.0034 |
| | | 875 | 1.86 | 0.86 | 1:0.0021 |
| | | 1100 | 1.86 | 1.06 | 1:0.0017 |
| | | 875 | 0.94 | 0.83 | 1:0.0011 |
| | | 1100 | 0.94 | 1.03 | 1:0.0009 |
| Ps. aeruginosa ATCC # 9027 | 24 hrs | 100 | — | — | — |
| | | — | 75 | — | — |
| | | 55 | 37.5 | 1.05 | 1:0.6818 |
| | | 55 | 9.4 | 0.68 | 1:0.1709 |
| | | 100 | 9.4 | 1.13 | 1:0.0940 |
| | | 55 | 4.6 | 0.61 | 1:0.0836 |
| | | 100 | 4.6 | 1.06 | 1:0.0460 |
| | 48 hrs | 100 | — | — | — |
| | | — | 125 | — | — |
| | | 21.25 | 75 | 0.81 | 1:3.5294 |
| | | 26.25 | 75 | 0.86 | 1:2.8571 |
| | | 32.5 | 75 | 0.93 | 1:2.3077 |
| | | 43.75 | 75 | 1.04 | 1:1.7143 |
| | | 55 | 37.5 | 0.85 | 1:0.6818 |
| | | 100 | 9.4 | 1.08 | 1:0.0940 |
| | | 100 | 4.6 | 1.04 | 1:0.0460 |
| S. aureus ATCC # 6538 | 24 hrs | 55 | — | — | — |
| | | — | 30 | — | — |
| | | 21.25 | 15 | 0.89 | 1:0.7059 |
| | | 26.25 | 15 | 0.98 | 1:0.5714 |
| | | 32.5 | 15 | 1.09 | 1:0.4615 |
| | | 26.25 | 7.5 | 0.73 | 1:0.2857 |
| | | 32.5 | 7.5 | 0.84 | 1:0.2308 |
| | | 43.75 | 7.5 | 1.05 | 1:0.1714 |
| | | 43.75 | 3.8 | 0.92 | 1:0.0869 |
| | | 55 | 3.8 | 1.13 | 1:0.0691 |
| | | 55 | 1.8 | 1.06 | 1:0.0327 |
| | | 55 | 0.94 | 1.03 | 1:0.0171 |
| | 48 hrs | 55 | — | — | — |
| | | — | 30 | — | — |
| | | 21.25 | 15 | 0.89 | 1:0.7059 |
| | | 26.25 | 15 | 0.98 | 1:0.5714 |
| | | 32.5 | 15 | 1.09 | 1:0.4615 |
| | | 26.25 | 7.5 | 0.73 | 1:0.2857 |
| | | 32.5 | 7.5 | 0.84 | 1:0.2308 |
| | | 43.75 | 7.5 | 1.05 | 1:0.1714 |
| | | 43.75 | 3.8 | 0.92 | 1:0.0869 |
| | | 55 | 3.8 | 1.13 | 1:0.0691 |
| | | 55 | 1.8 | 1.06 | 1:0.0327 |
| | | 55 | 0.94 | 1.03 | 1:0.0171 |

Ca: ppm AI of BIOBAN 1135 (4,4-dimethyloxazolidine)
Cb: ppm AI of MBIT(N-methyl-1,2-benzisothiazolin-3-one)
Ratio: Ca:Cb

TABLE 3

| Test Organisms | Contact Time | Ca | Cb | S.I. | Ca:Cb |
|---|---|---|---|---|---|
| A. niger ATCC # 16404 | 3 days | 875 | — | — | — |
| | | — | 75 | — | — |
| | | 425 | 18.8 | 0.74 | 1:0.0442 |
| | | 525 | 18.8 | 0.85 | 1:0.0358 |
| | | 650 | 18.8 | 0.99 | 1:0.0289 |
| | | 425 | 9.4 | 0.61 | 1:0.0221 |
| | | 525 | 9.4 | 0.73 | 1:0.0179 |
| | | 650 | 9.4 | 0.87 | 1:0.0145 |
| | | 875 | 9.4 | 1.13 | 1:0.0107 |
| | | 650 | 4.7 | 0.81 | 1:0.0072 |
| | | 875 | 4.7 | 1.06 | 1:0.0054 |
| | | 525 | 2.4 | 0.63 | 1:0.0046 |
| | | 650 | 2.4 | 0.77 | 1:0.0037 |
| | | 875 | 2.4 | 1.03 | 1:0.0027 |
| | | 650 | 1.2 | 0.76 | 1:0.0018 |
| | | 875 | 1.2 | 1.02 | 1:0.0014 |
| | 7 days | 1100 | — | — | — |
| | | — | 150 | — | — |
| | | 110 | 75 | 0.60 | 1:0.6818 |
| | | 200 | 75 | 0.68 | 1:0.3750 |
| | | 300 | 75 | 0.77 | 1:0.2500 |
| | | 425 | 75 | 0.89 | 1:0.1765 |
| | | 525 | 75 | 0.98 | 1:0.1429 |
| | | 650 | 75 | 1.09 | 1:0.1154 |
| | | 425 | 37.5 | 0.64 | 1:0.0882 |
| | | 525 | 37.5 | 0.73 | 1:0.0714 |
| | | 650 | 37.5 | 0.84 | 1:0.0577 |
| | | 875 | 37.5 | 1.05 | 1:0.0429 |
| | | 525 | 18.8 | 0.6 | 1:0.0358 |
| | | 650 | 18.8 | 0.72 | 1:0.0289 |
| | | 875 | 18.8 | 0.92 | 1:0.0215 |
| | | 1100 | 18.8 | 1.13 | 1:0.0171 |
| | | 525 | 9.4 | 0.54 | 1:0.0179 |
| | | 650 | 9.4 | 0.65 | 1:0.0145 |
| | | 875 | 9.4 | 0.86 | 1:0.0107 |
| | | 1100 | 9.4 | 1.06 | 1:0.0085 |
| | | 650 | 4.7 | 0.62 | 1:0.0072 |
| | | 875 | 4.7 | 0.83 | 1:0.0054 |

TABLE 3-continued

| Test Organisms | Contact Time | Ca | Cb | S.I. | Ca:Cb |
|---|---|---|---|---|---|
| | | 1100 | 4.7 | 1.03 | 1:0.0043 |
| | | 650 | 2.4 | 0.61 | 1:0.0037 |
| | | 875 | 2.4 | 0.81 | 1:0.0027 |
| | | 1100 | 2.4 | 1.02 | 1:0.0022 |
| | | 650 | 1.2 | 0.60 | 1:0.0018 |
| | | 875 | 1.2 | 0.80 | 1:0.0014 |
| | | 1100 | 1.2 | 1.01 | 1:0.0011 |
| *C. albicans* ATCC # 10231 | 48 hrs | 3000 | — | — | — |
| | | — | 30 | — | — |
| | | 525 | 15 | 0.68 | 1:0.0286 |
| | | 650 | 15 | 0.72 | 1:0.0231 |
| | | 875 | 15 | 0.79 | 1:0.0171 |
| | | 1100 | 15 | 0.87 | 1:0.0136 |
| | | 2000 | 15 | 1.17 | 1:0.0075 |
| | | 525 | 7.5 | 0.43 | 1:0.0143 |
| | | 650 | 7.5 | 0.47 | 1:0.0115 |
| | | 875 | 7.5 | 0.54 | 1:0.0086 |
| | | 1100 | 7.5 | 0.62 | 1:0.0068 |
| | | 2000 | 7.5 | 0.92 | 1:0.0038 |
| | | 3000 | 7.5 | 1.25 | 1:0.0025 |
| | | 875 | 3.75 | 0.42 | 1:0.0043 |
| | | 1100 | 3.75 | 0.49 | 1:0.0034 |
| | | 2000 | 3.75 | 0.79 | 1:0.0019 |
| | | 3000 | 3.75 | 1.13 | 1:0.0013 |
| | | 2000 | 1.86 | 0.73 | 1:0.0009 |
| | | 3000 | 1.86 | 1.06 | 1:0.0006 |
| | | 2000 | 0.94 | 0.70 | 1:0.0005 |
| | | 3000 | 0.94 | 1.03 | 1:0.0003 |
| | 72 hrs | 3000 | — | — | — |
| | | — | 30 | — | — |
| | | 525 | 15 | 0.68 | 1:0.0286 |
| | | 650 | 15 | 0.72 | 1:0.0231 |
| | | 875 | 15 | 0.79 | 1:0.0171 |
| | | 1100 | 15 | 0.87 | 1:0.0136 |
| | | 2000 | 15 | 1.17 | 1:0.0075 |
| | | 3000 | 15 | 1.5 | 1:0.0050 |
| | | 525 | 7.5 | 0.43 | 1:0.0143 |
| | | 650 | 7.5 | 0.47 | 1:0.0115 |
| | | 875 | 7.5 | 0.54 | 1:0.0086 |
| | | 1100 | 7.5 | 0.62 | 1:0.0068 |
| | | 2000 | 7.5 | 0.92 | 1:0.0038 |
| | | 3000 | 7.5 | 1.25 | 1:0.0025 |
| | | 875 | 3.75 | 0.42 | 1:0.0043 |
| | | 1100 | 3.75 | 0.49 | 1:0.0034 |
| | | 2000 | 3.75 | 0.79 | 1:0.0019 |
| | | 3000 | 3.75 | 1.13 | 1:0.0013 |
| | | 2000 | 1.86 | 0.73 | 1:0.0009 |
| | | 3000 | 1.86 | 1.06 | 1:0.0006 |
| | | 2000 | 0.94 | 0.70 | 1:0.0005 |
| | | 3000 | 0.94 | 1.03 | 1:0.0003 |
| *Ps. aeruginosa* ATCC # 9027 | 24 hrs | 87.5 | — | — | — |
| | | — | 75 | — | — |
| | | 65 | 9.4 | 0.87 | 1:0.1446 |
| | | 87.5 | 9.4 | 1.13 | 1:0.1074 |
| | 48 hrs | 110 | — | — | — |
| | | — | 125 | — | — |
| | | 87.5 | 9.4 | 0.87 | 1:0.1074 |
| | | 110 | 9.4 | 1.08 | 1:0.0855 |
| | | 110 | 4.6 | 1.04 | 1:0.0418 |
| *S. aureus* ATCC # 6538 | 24 hrs | 110 | — | — | — |
| | | — | 15 | — | — |
| | | 30 | 7.5 | 0.77 | 1:0.2500 |
| | | 42.5 | 7.5 | 89 | 1:0.1765 |
| | | 52.5 | 7.5 | 98 | 1:0.1429 |
| | | 65 | 7.5 | 1.09 | 1:0.1154 |
| | | 52.5 | 3.8 | 0.73 | 1:0.0724 |
| | | 65 | 3.8 | 0.84 | 1:0.0585 |
| | | 87.5 | 3.8 | 1.05 | 1:0.0434 |
| | | 110 | 0.94 | 1.06 | 1:0.0085 |
| | 48 hrs | 110 | — | — | — |
| | | — | 30 | — | — |
| | | 6.5 | 15 | 0.56 | 1:2.3077 |
| | | 8.75 | 15 | 0.58 | 1:1.7143 |
| | | 11 | 15 | 0.6 | 1:1.3636 |
| | | 20 | 15 | 0.68 | 1:0.7500 |
| | | 30 | 15 | 0.77 | 1:0.5000 |
| | | 42.5 | 15 | 0.89 | 1:0.3529 |
| | | 52.5 | 15 | 0.98 | 1:0.2857 |
| | | 65 | 15 | 1.09 | 1:0.2308 |
| | | 42.5 | 7.5 | 0.64 | 1:0.1765 |
| | | 52.5 | 7.5 | 0.73 | 1:0.1429 |
| | | 65 | 7.5 | 0.84 | 1:0.1154 |
| | | 87.5 | 7.5 | 1.05 | 1:0.0857 |
| | | 65 | 3.8 | 0.72 | 1:0.0585 |
| | | 110 | 1.8 | 1.06 | 1:0.0164 |
| | | 110 | 0.94 | 1.03 | 1:0.0085 |

Ca: ppm AI of SUTTOCIDE A (sodium hydroxymethylglycinate)
Cb: ppm AI of MBIT(N-methyl-1,2-benzisothiazolin-3-one)
Ratio: Ca:Cb

TABLE 4

| Test Organisms | Contact Time | Ca | Cb | S.I. | Ca:Cb |
|---|---|---|---|---|---|
| *A. niger* ATCC # 16404 | 3 days | 1100 | — | — | — |
| | | — | 37.5 | — | — |
| | | 425 | 18.8 | 0.89 | 1:0.0442 |
| | | 525 | 18.8 | 0.98 | 1:0.0358 |
| | | 650 | 18.8 | 1.09 | 1:0.0289 |
| | | 525 | 9.4 | 0.73 | 1:0.0179 |
| | | 650 | 9.4 | 0.84 | 1:0.0145 |
| | | 875 | 9.4 | 1.05 | 1:0.0107 |
| | | 1100 | 2.4 | 1.06 | 1:0.0022 |
| | | 1100 | 1.2 | 1.03 | 1:0.0011 |
| | 7 days | 1100 | — | — | — |
| | | — | 150 | — | — |
| | | 2 | 75 | 0.50 | 1:37.5000 |
| | | 20 | 75 | 0.52 | 1:3.7500 |
| | | 200 | 75 | 0.68 | 1:0.3750 |
| | | 525 | 75 | 0.98 | 1:0.1429 |
| | | 650 | 75 | 1.09 | 1:0.1154 |
| | | 20 | 37.5 | 0.27 | 1:1.8750 |
| | | 52.5 | 37.5 | 0.3 | 1:0.7143 |
| | | 87.5 | 37.5 | 0.33 | 1:0.4286 |
| | | 200 | 37.5 | 0.43 | 1:0.1875 |
| | | 425 | 37.5 | 0.64 | 1:0.0882 |
| | | 650 | 37.5 | 0.84 | 1:0.0577 |
| | | 875 | 37.5 | 1.05 | 1:0.0429 |
| | | 650 | 18.8 | 0.72 | 1:0.0289 |
| | | 875 | 18.8 | 0.92 | 1:0.0215 |
| | | 1100 | 18.8 | 1.13 | 1:0.0171 |
| | | 650 | 9.4 | 0.65 | 1:0.0145 |
| | | 875 | 9.4 | 0.86 | 1:0.0107 |
| | | 1100 | 9.4 | 1.06 | 1:0.0085 |
| | | 1100 | 4.7 | 1.03 | 1:0.0043 |
| | | 1100 | 2.4 | 1.02 | 1:0.0022 |
| | | 1100 | 1.2 | 1.01 | 1:0.0011 |
| *C. albicans* ATCC # 10231 | 48 hrs | 1100 | — | — | — |
| | | — | 30 | — | — |
| | | 525 | 15 | 0.98 | 1:0.0286 |
| | | 650 | 15 | 1.09 | 1:0.0231 |
| | | 525 | 7.5 | 0.73 | 1:0.0143 |
| | | 650 | 7.5 | 0.84 | 1:0.0115 |
| | | 875 | 7.5 | 1.05 | 1:0.0086 |
| | | 650 | 3.75 | 0.72 | 1:0.0058 |
| | | 875 | 3.75 | 0.92 | 1:0.0043 |
| | | 1100 | 3.75 | 1.13 | 1:0.0034 |
| | | 875 | 1.86 | 0.86 | 1:0.0021 |
| | | 1100 | 1.86 | 1.06 | 1:0.0017 |
| | | 875 | 0.94 | 0.83 | 1:0.0011 |
| | | 1100 | 0.94 | 1.03 | 1:0.0009 |
| | 72 hrs | 1100 | — | — | — |
| | | — | 60 | — | — |
| | | 2 | 30 | 0.50 | 1:15.0000 |
| | | 20 | 30 | 0.52 | 1:1.5000 |
| | | 110 | 30 | 0.60 | 1:0.2727 |
| | | 200 | 30 | 0.68 | 1:0.1500 |
| | | 300 | 30 | 0.77 | 1:0.1000 |
| | | 425 | 30 | 0.89 | 1:0.0706 |
| | | 525 | 30 | 0.98 | 1:0.0571 |

TABLE 4-continued

| Test Organisms | Contact Time | Ca | Cb | S.I. | Ca:Cb |
|---|---|---|---|---|---|
| | | 650 | 30 | 1.09 | 1:0.0462 |
| | | 525 | 15 | 0.73 | 1:0.0286 |
| | | 650 | 15 | 0.84 | 1:0.0231 |
| | | 525 | 7.5 | 0.6 | 1:0.0143 |
| | | 650 | 7.5 | 0.72 | 1:0.0115 |
| | | 875 | 7.5 | 0.92 | 1:0.0086 |
| | | 650 | 3.75 | 0.65 | 1:0.0058 |
| | | 875 | 3.75 | 0.86 | 1:0.0043 |
| | | 1100 | 3.75 | 1.06 | 1:0.0034 |
| | | 875 | 1.86 | 0.83 | 1:0.0021 |
| | | 1100 | 1.86 | 1.03 | 1:0.0017 |
| | | 875 | 0.94 | 0.81 | 1:0.0011 |
| | | 1100 | 0.94 | 1.02 | 1:0.0009 |
| *Ps. aeruginosa* ATCC # 9027 | 24 hrs | 425 | — | — | — |
| | | — | 75 | — | — |
| | | 425 | 4.6 | 1.06 | 1:0.0108 |
| | 48 hrs | 525 | — | — | — |
| | | — | 125 | — | — |
| | | 525 | 4.6 | 1.04 | 1:0.0088 |
| *S. aureus* ATCC # 6538 | 24 hrs | 10 | — | — | — |
| | | — | 15 | — | — |
| | | 2.625 | 7.5 | 0.76 | 1:2.8571 |
| | | 3.25 | 7.5 | 0.83 | 1:2.3077 |
| | | 4.375 | 7.5 | 0.94 | 1:1.7143 |
| | | 5.5 | 7.5 | 1.05 | 1:1.3636 |
| | | 4.375 | 3.8 | 0.69 | 1:0.8686 |
| | | 5.5 | 3.8 | 0.80 | 1:0.6909 |
| | | 10 | 3.8 | 1.25 | 1:0.3800 |
| | | 4.375 | 1.8 | 0.56 | 1:0.4114 |
| | | 5.5 | 1.8 | 0.67 | 1:0.3273 |
| | | 10 | 1.8 | 1.12 | 1:0.1800 |
| | | 10 | 0.94 | 1.06 | 1:0.0940 |
| | 48 hrs | 10 | — | — | — |
| | | — | 30 | — | — |
| | | 0.1 | 15 | 0.51 | 1:150.0000 |
| | | 0.5 | 15 | 0.55 | 1:30.0000 |
| | | 1 | 15 | 0.6 | 1:15.0000 |
| | | 1.5 | 15 | 0.65 | 1:10.0000 |
| | | 2.125 | 15 | 0.71 | 1:7.0588 |
| | | 2.625 | 15 | 0.76 | 1:5.7143 |
| | | 3.25 | 15 | 0.83 | 1:4.6154 |
| | | 4.375 | 15 | 0.94 | 1:3.4286 |
| | | 5.5 | 15 | 1.05 | 1:2.7273 |
| | | 4.375 | 7.5 | 0.69 | 1:1.7143 |
| | | 5.5 | 7.5 | 0.80 | 1:1.3636 |
| | | 10 | 7.5 | 1.25 | 1:0.7500 |
| | | 4.375 | 3.8 | 0.56 | 1:0.8686 |
| | | 5.5 | 3.8 | 0.68 | 1:0.6909 |
| | | 10 | 3.8 | 1.13 | 1:0.3800 |
| | | 5.5 | 1.8 | 0.61 | 1:0.3273 |
| | | 10 | 1.8 | 1.06 | 1:0.1800 |
| | | 10 | 0.94 | 1.03 | 1:0.0940 |

Ca: ppm AI of Phospholipid PTM(myristamidopropyl PG-dimoonium chloride phosphate)
Cb: ppm AI of MBIT(N-methyl-1,2-benzisothiazolin-3-one)
Ratio: Ca:Cb

TABLE 5

| Test Organisms | Contact Time | Ca | Cb | S.I. | Ca:Cb |
|---|---|---|---|---|---|
| *A. niger* ATCC # 16404 | 3 days | 650 | — | — | — |
| | | — | 75 | — | — |
| | | 425 | 18.8 | 0.9 | 1:0.0442 |
| | | 525 | 18.8 | 1.06 | 1:0.0358 |
| | | 525 | 9.4 | 0.93 | 1:0.0179 |
| | | 650 | 9.4 | 1.13 | 1:0.0145 |
| | | 525 | 4.7 | 0.87 | 1:0.0090 |
| | | 525 | 2.4 | 0.84 | 1:0.0046 |
| | | 650 | 2.4 | 1.03 | 1:0.0037 |
| | | 650 | 1.2 | 1.02 | 1:0.0018 |
| | 7 days | 875 | — | — | — |
| | | — | 150 | — | — |
| | | 110 | 75 | 0.63 | 1:0.6818 |

TABLE 5-continued

| Test Organisms | Contact Time | Ca | Cb | S.I. | Ca:Cb |
|---|---|---|---|---|---|
| | | 200 | 75 | 0.73 | 1:0.3750 |
| | | 300 | 75 | 0.84 | 1:0.2500 |
| | | 425 | 75 | 0.99 | 1:0.1765 |
| | | 650 | 37.5 | 0.99 | 1:0.0577 |
| | | 425 | 18.8 | 0.61 | 1:0.0442 |
| | | 650 | 18.8 | 0.87 | 1:0.0289 |
| | | 875 | 18.8 | 1.13 | 1:0.0215 |
| | | 875 | 9.4 | 1.06 | 1:0.0107 |
| | | 875 | 4.7 | 1.03 | 1:0.0054 |
| | | 875 | 2.4 | 1.02 | 1:0.0027 |
| | | 875 | 1.2 | 1.01 | 1:0.0014 |
| *C. albicans* ATCC # 10231 | 48 hrs | 65 | — | — | — |
| | | — | 30 | — | — |
| | | 42.5 | 7.5 | 0.9 | 1:0.1765 |
| | | 52.5 | 7.5 | 1.06 | 1:0.1429 |
| | | 65 | 1.86 | 1.06 | 1:0.0286 |
| | | 65 | 0.94 | 1.03 | 1:0.0145 |
| | 72 hrs | 87.5 | — | — | — |
| | | — | 30 | — | — |
| | | 42.5 | 15 | 0.99 | 1:0.3529 |
| | | 42.5 | 7.5 | 0.74 | 1:0.1765 |
| | | 52.5 | 7.5 | 0.85 | 1:0.1429 |
| | | 65 | 7.5 | 0.99 | 1:0.1154 |
| | | 65 | 3.75 | 0.87 | 1:0.0577 |
| | | 87.5 | 3.75 | 1.13 | 1:0.0429 |
| | | 87.5 | 1.86 | 1.06 | 1:0.0213 |
| | | 87.5 | 0.94 | 1.03 | 1:0.0107 |
| *Ps. aeruginosa* ATCC # 9027 | 48 hrs | >11000 | — | — | — |
| | | — | 125 | — | — |
| | | 8750 | 75 | 1.4 | 1:0.0086 |
| | | 11000 | 37.5 | 1.3 | 1:0.0034 |
| | | 11000 | 18.75 | 1.15 | 1:0.0017 |
| | | 11000 | 9.4 | 1.08 | 1:0.0009 |
| | | 11000 | 4.6 | 1.04 | 1:0.0004 |
| *S. aureus* ATCC # 6538 | 24 hrs | 425 | — | — | — |
| | | — | 15 | — | — |
| | | 425 | 0.94 | 1.06 | 1:0.0022 |
| | 48 hrs | 425 | — | — | — |
| | | — | 30 | — | — |
| | | 425 | 1.8 | 1.06 | 1:0.0042 |
| | | 425 | 0.94 | 1.03 | 1:0.0022 |

Ca: ppm AI of Caprylic acid (octanoic acid)
Cb: ppm AI of MBIT(N-methyl-1,2-benzisothiazolin-3-one)
Ratio: Ca:Cb

TABLE 6

| Test Organisms | Contact Time | Ca | Cb | S.I. | Ca:Cb |
|---|---|---|---|---|---|
| *A. niger* ATCC # 16404 | 3 days | 875 | — | — | — |
| | | — | 37.5 | — | — |
| | | 650 | 9.4 | 0.99 | 1:0.0145 |
| | | 650 | 4.7 | 0.87 | 1:0.0072 |
| | | 875 | 4.7 | 1.13 | 1:0.0054 |
| | | 875 | 2.4 | 1.06 | 1:0.0027 |
| | | 875 | 1.2 | 1.03 | 1:0.0014 |
| | 7 days | 1100 | — | — | — |
| | | — | 150 | — | — |
| | | 87.5 | 75 | 0.58 | 1:0.8571 |
| | | 110 | 75 | 0.60 | 1:0.6818 |
| | | 200 | 75 | 0.68 | 1:0.3750 |
| | | 300 | 75 | 0.77 | 1:0.2500 |
| | | 425 | 75 | 0.89 | 1:0.1765 |
| | | 525 | 75 | 0.98 | 1:0.1429 |
| | | 650 | 75 | 1.09 | 1:0.1154 |
| | | 650 | 37.5 | 0.84 | 1:0.0577 |
| | | 1100 | 9.4 | 1.06 | 1:0.0085 |
| | | 1100 | 4.7 | 1.03 | 1:0.0043 |
| | | 1100 | 2.4 | 1.02 | 1:0.0022 |
| | | 1100 | 1.2 | 1.01 | 1:0.0011 |
| *C. albicans* ATCC # 10231 | 48 hrs | 2000 | — | — | — |
| | | — | 30 | — | — |
| | | 6.5 | 15 | 0.50 | 1:2.3077 |

TABLE 6-continued

| Test Organisms | Contact Time | Ca | Cb | S.I. | Ca:Cb |
|---|---|---|---|---|---|
| | | 11 | 15 | 0.51 | 1:1.3636 |
| | | 110 | 15 | 0.56 | 1:0.1364 |
| | | 200 | 15 | 0.60 | 1:0.0750 |
| | | 300 | 15 | 0.65 | 1:0.0500 |
| | | 650 | 15 | 0.83 | 1:0.0231 |
| | | 875 | 15 | 0.94 | 1:0.0171 |
| | | 1100 | 15 | 1.05 | 1:0.0136 |
| | | 2000 | 1.86 | 1.06 | 1:0.0009 |
| | | 2000 | 0.94 | 1.03 | 1:0.0005 |
| | 72 hrs | 2000 | — | — | — |
| | | — | 30 | — | — |
| | | 425 | 15 | 0.71 | 1:0.0353 |
| | | 525 | 15 | 0.76 | 1:0.0286 |
| | | 650 | 15 | 0.83 | 1:0.0231 |
| | | 875 | 15 | 0.94 | 1:0.0171 |
| | | 1100 | 15 | 1.05 | 1:0.0136 |
| | | 2000 | 1.86 | 1.06 | 1:0.0009 |
| | | 2000 | 0.94 | 1.03 | 1:0.0005 |
| Ps. aeruginosa ATCC # 9027 | 24 hrs | 11000 | — | — | — |
| | | — | 75 | — | — |
| | | 8750 | 37.5 | 1.3 | 1:0.0043 |
| | 48 hrs | 11000 | — | — | — |
| | | — | 125 | — | — |
| | | 4250 | 75 | 0.99 | 1:0.0176 |
| S. aureus ATCC # 6538 | 24 hrs | 2000 | — | — | — |
| | | — | 30 | — | — |
| | | 8.75 | 15 | 0.5 | 1:1.7143 |
| | | 20 | 15 | 0.51 | 1:0.7500 |
| | | 42.5 | 15 | 0.52 | 1:0.3529 |
| | | 65 | 15 | 0.53 | 1:0.2308 |
| | | 110 | 15 | 0.56 | 1:0.1364 |
| | | 200 | 15 | 0.6 | 1:0.0750 |
| | | 425 | 15 | 0.71 | 1:0.0353 |
| | | 525 | 15 | 0.76 | 1:0.0286 |
| | | 650 | 15 | 0.83 | 1:0.0231 |
| | | 875 | 15 | 0.94 | 1:0.0171 |
| | | 1100 | 15 | 1.05 | 1:0.0136 |
| | | 2000 | 1.8 | 1.06 | 1:0.0009 |
| | | 2000 | 0.94 | 1.03 | 1:0.0005 |
| | 48 hrs | 2000 | — | — | — |
| | | — | 30 | — | — |
| | | 8.75 | 15 | 0.50 | 1:1.7143 |
| | | 20 | 15 | 0.51 | 1:0.7500 |
| | | 42.5 | 15 | 0.52 | 1:0.3529 |
| | | 65 | 15 | 0.53 | 1:0.2308 |
| | | 110 | 15 | 0.56 | 1:0.1364 |
| | | 200 | 15 | 0.60 | 1:0.0750 |
| | | 425 | 15 | 0.71 | 1:0.0353 |
| | | 525 | 15 | 0.76 | 1:0.0286 |
| | | 650 | 15 | 0.83 | 1:0.0231 |
| | | 875 | 15 | 0.94 | 1:0.0171 |
| | | 1100 | 15 | 1.05 | 1:0.0136 |
| | | 2000 | 1.8 | 1.06 | 1:0.0009 |
| | | 2000 | 0.94 | 1.03 | 1:0.0005 |

Ca: ppm AI of SENSIVA SC 50(3[(2-ethylhexyl)oxy]1,2-propanediol) (2- ethylhexyl glycerin)
Cb: ppm AI of MBIT(N-methyl-1,2-benzisothiazolin-3-one)
Ratio: Ca:Cb

TABLE 7

| Test Organisms | Contact Time | Ca | Cb | S.I. | Ca:Cb |
|---|---|---|---|---|---|
| A. niger ATCC # 16404 | 3 days | 4250 | — | — | — |
| | | — | 75 | — | — |
| | | 2000 | 37.5 | 0.97 | 1:0.0188 |
| | | 3000 | 37.5 | 1.21 | 1:0.0125 |
| | | 2000 | 18.8 | 0.72 | 1:0.0094 |
| | | 3000 | 18.8 | 0.96 | 1:0.0063 |
| | | 4250 | 18.8 | 1.25 | 1:0.0044 |
| | | 2000 | 9.4 | 0.60 | 1:0.0047 |
| | | 3000 | 9.4 | 0.83 | 1:0.0031 |
| | | 4250 | 9.4 | 1.13 | 1:0.0022 |
| | | 2000 | 4.7 | 0.53 | 1:0.0024 |

TABLE 7-continued

| Test Organisms | Contact Time | Ca | Cb | S.I. | Ca:Cb |
|---|---|---|---|---|---|
| | | 3000 | 4.7 | 0.77 | 1:0.0016 |
| | | 4250 | 4.7 | 1.06 | 1:0.0011 |
| | | 2000 | 2.4 | 0.5 | 1:0.0012 |
| | | 3000 | 2.4 | 0.74 | 1:0.0008 |
| | | 4250 | 2.4 | 1.03 | 1:0.0006 |
| | | 3000 | 1.2 | 0.72 | 1:0.0004 |
| | | 4250 | 1.2 | 1.02 | 1:0.0003 |
| | 7 days | 4250 | — | — | — |
| | | — | 150 | — | — |
| | | 1100 | 75 | 0.76 | 1:0.0682 |
| | | 2000 | 75 | 0.97 | 1:0.0375 |
| | | 3000 | 75 | 1.21 | 1:0.0250 |
| | | 2000 | 37.5 | 0.72 | 1:0.0188 |
| | | 3000 | 37.5 | 0.96 | 1:0.0125 |
| | | 4250 | 37.5 | 1.25 | 1:0.0088 |
| | | 2000 | 18.8 | 0.60 | 1:0.0094 |
| | | 3000 | 18.8 | 0.83 | 1:0.0063 |
| | | 4250 | 18.8 | 1.13 | 1:0.0044 |
| | | 2000 | 9.4 | 0.53 | 1:0.0047 |
| | | 3000 | 9.4 | 0.77 | 1:0.0031 |
| | | 4250 | 9.4 | 1.06 | 1:0.0022 |
| | | 2000 | 4.7 | 0.50 | 1:0.0024 |
| | | 3000 | 4.7 | 0.74 | 1:0.0016 |
| | | 4250 | 4.7 | 1.03 | 1:0.0011 |
| | | 2000 | 2.4 | 0.49 | 1:0.0012 |
| | | 3000 | 2.4 | 0.72 | 1:0.0008 |
| | | 4250 | 2.4 | 1.02 | 1:0.0006 |
| C. albicans ATCC # 10231 | 48 hrs | 200 | — | — | — |
| | | — | 30 | — | — |
| | | 0.2 | 15 | 0.50 | 1:75.0000 |
| | | 2 | 15 | 0.51 | 1:7.5000 |
| | | 20 | 15 | 0.60 | 1:0.7500 |
| | | 42.5 | 15 | 0.71 | 1:0.3529 |
| | | 65 | 15 | 0.83 | 1:0.2308 |
| | | 87.5 | 15 | 0.94 | 1:0.1714 |
| | | 110 | 15 | 1.05 | 1:0.1364 |
| | | 200 | 1.86 | 1.06 | 1:0.0093 |
| | | 200 | 0.94 | 1.03 | 1:0.0047 |
| | 72 hrs | 200 | — | — | — |
| | | — | 30 | — | — |
| | | 0.2 | 15 | 0.50 | 1:75.0000 |
| | | 2 | 15 | 0.51 | 1:7.5000 |
| | | 20 | 15 | 0.6 | 1:0.7500 |
| | | 42.5 | 15 | 0.71 | 1:0.3529 |
| | | 65 | 15 | 0.83 | 1:0.2308 |
| | | 87.5 | 15 | 0.94 | 1:0.1714 |
| | | 110 | 15 | 1.05 | 1:0.1364 |
| | | 200 | 1.86 | 1.06 | 1:0.0093 |
| | | 200 | 0.94 | 1.03 | 1:0.0047 |
| Ps. aeruginosa ATCC # 9027 | 48 hrs | >11000 | — | — | — |
| | | — | 125 | — | — |
| | | 2000 | 75 | 0.78 | 1:0.0375 |
| | | 3000 | 75 | 0.87 | 1:0.0250 |
| | | 4250 | 75 | 0.99 | 1:0.0176 |
| S. aureus ATCC # 6538 | 24 hrs | 650 | — | — | — |
| | | — | 30 | — | — |
| | | 0.2 | 15 | 0.50 | 1:75.0000 |
| | | 2 | 15 | 0.50 | 1:7.5000 |
| | | 6.5 | 15 | 0.51 | 1:2.3077 |
| | | 11 | 15 | 0.52 | 1:1.3636 |
| | | 20 | 15 | 0.53 | 1:0.7500 |
| | | 30 | 15 | 0.55 | 1:0.5000 |
| | | 42.5 | 15 | 0.57 | 1:0.3529 |
| | | 52.5 | 15 | 0.58 | 1:0.2857 |
| | | 65 | 15 | 0.60 | 1:0.2308 |
| | | 87.5 | 15 | 0.63 | 1:0.1714 |
| | | 110 | 15 | 0.67 | 1:0.1364 |
| | | 200 | 15 | 0.81 | 1:0.0750 |
| | | 300 | 15 | 0.96 | 1:0.0500 |
| | | 425 | 15 | 1.15 | 1:0.0353 |
| | | 425 | 7.5 | 0.9 | 1:0.0176 |
| | | 525 | 7.5 | 1.06 | 1:0.0143 |
| | 48 hrs | 875 | — | — | — |
| | | — | 30 | — | — |
| | | 0.2 | 15 | 0.50 | 1:75.0000 |
| | | 2 | 15 | 0.50 | 1:7.5000 |
| | | 6.5 | 15 | 0.51 | 1:2.3077 |

TABLE 7-continued

| Test Organisms | Contact Time | Ca | Cb | S.I. | Ca:Cb |
|---|---|---|---|---|---|
| | | 11 | 15 | 0.51 | 1:1.3636 |
| | | 20 | 15 | 0.52 | 1:0.7500 |
| | | 30 | 15 | 0.53 | 1:0.5000 |
| | | 42.5 | 15 | 0.55 | 1:0.3529 |
| | | 52.5 | 15 | 0.56 | 1:0.2857 |
| | | 65 | 15 | 0.57 | 1:0.2308 |
| | | 87.5 | 15 | 0.60 | 1:0.1714 |
| | | 110 | 15 | 0.63 | 1:0.1364 |
| | | 200 | 15 | 0.73 | 1:0.0750 |
| | | 300 | 15 | 0.84 | 1:0.0500 |
| | | 425 | 15 | 0.99 | 1:0.0353 |
| | | 650 | 7.5 | 0.99 | 1:0.0115 |
| | | 875 | 1.8 | 1.06 | 1:0.0021 |
| | | 875 | 0.94 | 1.03 | 1:0.0011 |

Ca: ppm AI of CAPMUL MCM C8 (glyceryl monocaprylate)
Cb: ppm AI of MBIT (N-methyl-1,2-benzisothiazolin-3-one)
Ratio: Ca:Cb

TABLE 8

| Test Organisms | Contact Time | Ca | Cb | S.I. | Ca:Cb |
|---|---|---|---|---|---|
| A. niger ATCC # 16404 | 3 days | 2000 | — | — | — |
| | | — | 75 | — | — |
| | | 4.25 | 37.5 | 0.50 | 1:8.8235 |
| | | 6.5 | 37.5 | 0.50 | 1:5.7692 |
| | | 11 | 37.5 | 0.51 | 1:3.4091 |
| | | 30 | 37.5 | 0.52 | 1:1.2500 |
| | | 65 | 37.5 | 0.53 | 1:0.5769 |
| | | 110 | 37.5 | 0.56 | 1:0.3409 |
| | | 200 | 37.5 | 0.60 | 1:0.1875 |
| | | 300 | 37.5 | 0.65 | 1:0.1250 |
| | | 425 | 37.5 | 0.71 | 1:0.0882 |
| | | 525 | 37.5 | 0.76 | 1:0.0714 |
| | | 650 | 37.5 | 0.83 | 1:0.0577 |
| | | 875 | 37.5 | 0.94 | 1:0.0429 |
| | | 1100 | 37.5 | 1.05 | 1:0.0341 |
| | | 1100 | 18.8 | 0.8 | 1:0.0171 |
| | | 2000 | 4.7 | 1.06 | 1:0.0024 |
| | | 2000 | 2.4 | 1.03 | 1:0.0012 |
| | | 2000 | 1.2 | 1.02 | 1:0.0006 |
| | 7 days | 2000 | — | — | — |
| | | — | 150 | — | — |
| | | 525 | 75 | 0.76 | 1:0.1429 |
| | | 650 | 75 | 0.83 | 1:0.1154 |
| | | 875 | 75 | 0.94 | 1:0.0857 |
| | | 1100 | 75 | 1.05 | 1:0.0682 |
| | | 1100 | 37.5 | 0.8 | 1:0.0341 |
| | | 1100 | 18.8 | 0.68 | 1:0.0171 |
| | | 2000 | 9.4 | 1.06 | 1:0.0047 |
| | | 2000 | 4.7 | 1.03 | 1:0.0024 |
| | | 2000 | 2.4 | 1.02 | 1:0.0012 |
| | | 2000 | 1.2 | 1.01 | 1:0.0006 |
| C. albicans ATCC # 10231 | 48 hrs | 425 | — | — | — |
| | | — | 30 | — | — |
| | | 87.5 | 15 | 0.71 | 1:0.1714 |
| | | 110 | 15 | 0.76 | 1:0.1364 |
| | | 200 | 15 | 0.97 | 1:0.0750 |
| | | 300 | 15 | 1.21 | 1:0.0500 |
| | | 200 | 7.5 | 0.72 | 1:0.0375 |
| | | 300 | 7.5 | 0.96 | 1:0.0250 |
| | | 425 | 7.5 | 1.25 | 1:0.0176 |
| | | 200 | 3.75 | 0.60 | 1:0.0188 |
| | | 300 | 3.75 | 0.83 | 1:0.0125 |
| | | 425 | 3.75 | 1.13 | 1:0.0088 |
| | | 200 | 1.86 | 0.53 | 1:0.0093 |
| | | 300 | 1.86 | 0.77 | 1:0.0062 |
| | | 425 | 1.86 | 1.06 | 1:0.0044 |
| | | 200 | 0.94 | 0.50 | 1:0.0047 |
| | | 300 | 0.94 | 0.74 | 1:0.0031 |
| | | 425 | 0.94 | 1.03 | 1:0.0022 |

TABLE 8-continued

| Test Organisms | Contact Time | Ca | Cb | S.I. | Ca:Cb |
|---|---|---|---|---|---|
| | 72 hrs | 425 | — | — | — |
| | | — | 30 | — | — |
| | | 87.5 | 15 | 0.71 | 1:0.1714 |
| | | 110 | 15 | 0.76 | 1:0.1364 |
| | | 200 | 15 | 0.97 | 1:0.0750 |
| | | 300 | 15 | 1.21 | 1:0.0500 |
| | | 200 | 7.5 | 0.72 | 1:0.0375 |
| | | 300 | 7.5 | 0.96 | 1:0.0250 |
| | | 425 | 7.5 | 1.25 | 1:0.0176 |
| | | 200 | 3.75 | 0.60 | 1:0.0188 |
| | | 300 | 3.75 | 0.83 | 1:0.0125 |
| | | 425 | 3.75 | 1.13 | 1:0.0088 |
| | | 200 | 1.86 | 0.53 | 1:0.0093 |
| | | 300 | 1.86 | 0.77 | 1:0.0062 |
| | | 425 | 1.86 | 1.06 | 1:0.0044 |
| | | 200 | 0.94 | 0.50 | 1:0.0047 |
| | | 300 | 0.94 | 0.74 | 1:0.0031 |
| | | 425 | 0.94 | 1.03 | 1:0.0022 |
| Ps. aeruginosa ATCC # 9027 | 24 hrs | 11000 | — | — | — |
| | | — | 75 | — | — |
| | | — | 37.5 | — | — |
| | | — | 18.75 | — | — |
| | | — | 9.4 | — | — |
| | | — | 4.6 | — | — |
| | 48 hrs | 11000 | — | — | — |
| | | — | 125 | — | — |
| | | — | 75 | — | — |
| | | — | 37.5 | — | — |
| | | — | 18.75 | — | — |
| | | — | 9.4 | — | — |
| | | — | 4.6 | — | — |
| S. aureus ATCC # 6538 | 24 hrs | 200 | — | — | — |
| | | — | 30 | — | — |
| | | 5.25 | 15 | 0.53 | 1:2.8571 |
| | | 11 | 15 | 0.56 | 1:1.3636 |
| | | 20 | 15 | 0.60 | 1:0.7500 |
| | | 30 | 15 | 0.65 | 1:0.5000 |
| | | 42.5 | 15 | 0.71 | 1:0.3529 |
| | | 52.5 | 15 | 0.76 | 1:0.2857 |
| | | 65 | 15 | 0.83 | 1:0.2308 |
| | | 87.5 | 15 | 0.94 | 1:0.1714 |
| | | 110 | 15 | 1.05 | 1:0.1364 |
| | 48 hrs | 200 | — | — | — |
| | | — | 30 | — | — |
| | | 65 | 15 | 0.83 | 1:0.2308 |
| | | 87.5 | 15 | 0.94 | 1:0.1714 |
| | | 110 | 15 | 1.05 | 1:0.1364 |

Ca: ppm AI of CapmulMCM C10 (Mono/digyceride of capric acid (Glyceryl Monocaprate))
Cb: ppm AI of MBIT (N-methyl-1,2-benzisothiazolin-3-one)
Ratio: Ca:Cb

TABLE 9

| Test Organisms | Contact Time | Ca | Cb | S.I. | Ca:Cb |
|---|---|---|---|---|---|
| A. niger ATCC # 16404 | 3 days | 650 | — | — | — |
| | | — | 37.5 | — | — |
| | | 200 | 18.8 | 0.81 | 1:0.0940 |
| | | 300 | 18.8 | 0.96 | 1:0.0627 |
| | | 425 | 18.8 | 1.16 | 1:0.0442 |
| | | 425 | 9.4 | 0.90 | 1:0.0221 |
| | | 525 | 9.4 | 1.06 | 1:0.0179 |
| | | 425 | 4.7 | 0.78 | 1:0.0111 |
| | | 525 | 4.7 | 0.93 | 1:0.0090 |
| | | 650 | 4.7 | 1.13 | 1:0.0072 |
| | | 425 | 2.4 | 0.72 | 1:0.0056 |
| | | 525 | 2.4 | 0.87 | 1:0.0046 |
| | | 650 | 2.4 | 1.06 | 1:0.0037 |
| | | 425 | 1.2 | 0.69 | 1:0.0028 |
| | | 525 | 1.2 | 0.84 | 1:0.0023 |
| | | 650 | 1.2 | 1.03 | 1:0.0018 |

TABLE 9-continued

| Test Organisms | Contact Time | Ca | Cb | S.I. | Ca:Cb |
|---|---|---|---|---|---|
| | 7 days | 875 | — | — | — |
| | | — | 150 | — | — |
| | | 425 | 75 | 0.99 | 1:0.1765 |
| | | 650 | 37.5 | 0.99 | 1:0.0577 |
| | | 525 | 18.8 | 0.73 | 1:0.0358 |
| | | 650 | 18.8 | 0.87 | 1:0.0289 |
| | | 875 | 18.8 | 1.13 | 1:0.0215 |
| | | 875 | 9.4 | 1.06 | 1:0.0107 |
| | | 875 | 4.7 | 1.03 | 1:0.0054 |
| | | 875 | 2.5 | 1.02 | 1:0.0029 |
| | | 875 | 1.2 | 1.01 | 1:0.0014 |
| C. albicans ATCC # 10231 | 48 hrs | 3000 | — | — | — |
| | | — | 30 | — | — |
| | | 875 | 15 | 0.79 | 1:0.0171 |
| | | 1100 | 15 | 0.87 | 1:0.0136 |
| | | 2000 | 15 | 1.17 | 1:0.0075 |
| | | 875 | 7.5 | 0.54 | 1:0.0086 |
| | | 1100 | 7.5 | 0.62 | 1:0.0068 |
| | | 2000 | 7.5 | 0.92 | 1:0.0038 |
| | | 3000 | 7.5 | 1.25 | 1:0.0025 |
| | | 2000 | 3.75 | 0.79 | 1:0.0019 |
| | | 3000 | 3.75 | 1.13 | 1:0.0013 |
| | | 2000 | 1.86 | 0.73 | 1:0.0009 |
| | | 3000 | 1.86 | 1.06 | 1:0.0006 |
| | | 3000 | 0.94 | 1.03 | 1:0.0003 |
| | 72 hrs | 4250 | — | — | — |
| | | — | 30 | — | — |
| | | 875 | 15 | 0.71 | 1:0.0171 |
| | | 1100 | 15 | 0.76 | 1:0.0136 |
| | | 2000 | 15 | 0.97 | 1:0.0075 |
| | | 3000 | 15 | 1.21 | 1:0.0050 |
| | | 875 | 7.5 | 0.46 | 1:0.0086 |
| | | 1100 | 7.5 | 0.51 | 1:0.0068 |
| | | 2000 | 7.5 | 0.72 | 1:0.0038 |
| | | 3000 | 7.5 | 0.96 | 1:0.0025 |
| | | 4250 | 7.5 | 1.25 | 1:0.0018 |
| | | 2000 | 3.75 | 0.6 | 1:0.0019 |
| | | 3000 | 3.75 | 0.83 | 1:0.0013 |
| | | 4250 | 3.75 | 1.13 | 1:0.0009 |
| | | 2000 | 1.86 | 0.53 | 1:0.0009 |
| | | 3000 | 0.94 | 0.74 | 1:0.0003 |
| | | 4250 | 0.94 | 1.03 | 1:0.0002 |
| Ps. aeruginosa ATCC # 9027 | 24 hrs | 100 | — | — | — |
| | | — | 75 | — | — |
| | | 26.25 | 75 | 1.26 | 1:2.8571 |
| | | 43.75 | 37.5 | 0.94 | 1:0.8571 |
| | | 55 | 37.5 | 1.05 | 1:0.6818 |
| | | 55 | 18.75 | 0.80 | 1:0.3409 |
| | | 100 | 18.75 | 1.25 | 1:0.1875 |
| | | 55 | 9.4 | 0.68 | 1:0.1709 |
| | | 100 | 9.4 | 1.13 | 1:0.0940 |
| | | 100 | 4.6 | 1.06 | 1:0.0460 |
| | 48 hrs | 150 | — | — | — |
| | | — | 125 | — | — |
| | | 26.25 | 75 | 0.78 | 1:2.8571 |
| | | 32.5 | 75 | 0.82 | 1:2.3077 |
| | | 43.75 | 75 | 0.89 | 1:1.7143 |
| | | 55 | 75 | 0.97 | 1:1.3636 |
| | | 100 | 75 | 1.27 | 1:0.7500 |
| | | 55 | 37.5 | 0.67 | 1:0.6818 |
| | | 100 | 37.5 | 0.97 | 1:0.3750 |
| | | 150 | 37.5 | 1.3 | 1:0.2500 |
| | | 100 | 18.75 | 0.82 | 1:0.1875 |
| | | 150 | 18.75 | 1.15 | 1:0.1250 |
| | | 150 | 9.4 | 1.08 | 1:0.0627 |
| | | 150 | 4.6 | 1.04 | 1:0.0307 |
| S. aureus ATCC # 6538 | 24 hrs | 55 | — | — | — |
| | | — | 30 | — | — |
| | | 2.125 | 15 | 0.54 | 1:7.0588 |
| | | 5.5 | 15 | 0.60 | 1:2.7273 |
| | | 10 | 15 | 0.68 | 1:1.5000 |
| | | 26.25 | 15 | 0.98 | 1:0.5714 |
| | | 32.5 | 15 | 1.09 | 1:0.4615 |
| | | 21.25 | 7.5 | 0.64 | 1:0.3529 |
| | | 26.25 | 7.5 | 0.73 | 1:0.2857 |
| | | 32.5 | 7.5 | 0.84 | 1:0.2308 |
| | | 43.75 | 7.5 | 1.05 | 1:0.1714 |

TABLE 9-continued

| Test Organisms | Contact Time | Ca | Cb | S.I. | Ca:Cb |
|---|---|---|---|---|---|
| | | 32.5 | 3.8 | 0.72 | 1:0.1169 |
| | | 43.75 | 3.8 | 0.92 | 1:0.0869 |
| | | 55 | 3.8 | 1.13 | 1:0.0691 |
| | | 55 | 1.8 | 1.06 | 1:0.0327 |
| | | 55 | 0.94 | 1.03 | 1:0.0171 |
| | 48 hrs | 55 | — | — | — |
| | | — | 30 | — | — |
| | | 2.125 | 15 | 0.54 | 1:7.0588 |
| | | 5.5 | 15 | 0.60 | 1:2.7273 |
| | | 10 | 15 | 0.68 | 1:1.5000 |
| | | 26.25 | 15 | 0.98 | 1:0.5714 |
| | | 32.5 | 15 | 1.09 | 1:0.4615 |
| | | 21.25 | 7.5 | 0.64 | 1:0.3529 |
| | | 26.25 | 7.5 | 0.73 | 1:0.2857 |
| | | 32.5 | 7.5 | 0.84 | 1:0.2308 |
| | | 43.75 | 7.5 | 1.05 | 1:0.1714 |
| | | 32.5 | 3.8 | 0.72 | 1:0.1169 |
| | | 43.75 | 3.8 | 0.92 | 1:0.0869 |
| | | 55 | 3.8 | 1.13 | 1:0.0691 |
| | | 55 | 1.8 | 1.06 | 1:0.0327 |
| | | 55 | 0.94 | 1.03 | 1:0.0171 |

Ca: ppm AI of BIOBAN1246 (7α-ethyldihydro-1H, 3H, 5H-oxazolo (3,4-C) oxazole)
Cb: ppm AI of MBIT(N-methyl-1,2-benzisothiazolin-3-one)
Ratio: Ca:Cb

TABLE 10

| Test Organisms | Contact Time | Ca | Cb | S.I. | Ca:Cb |
|---|---|---|---|---|---|
| A. niger ATCC # 16404 | 3 days | 3 | — | — | — |
| | | — | 37.5 | — | — |
| | | 3 | 2.4 | 1.06 | 1:0.8000 |
| | | 3 | 1.2 | 1.03 | 1:0.4000 |
| | 7 days | 8.75 | — | — | — |
| | | — | 150 | — | — |
| | | 0.525 | 75 | 0.56 | 1:142.8571 |
| | | 0.65 | 75 | 0.57 | 1:115.3846 |
| | | 0.875 | 75 | 0.60 | 1:85.7143 |
| | | 1.1 | 75 | 0.63 | 1:68.1818 |
| | | 2 | 75 | 0.73 | 1:37.5000 |
| | | 3 | 75 | 0.84 | 1:25.0000 |
| | | 4.25 | 75 | 0.99 | 1:17.6471 |
| | | 8.75 | 9.4 | 1.06 | 1:1.0743 |
| | | 6.5 | 2.4 | 0.76 | 1:0.3692 |
| | | 8.75 | 2.4 | 1.02 | 1:0.2743 |
| | | 8.75 | 1.2 | 1.01 | 1:0.1371 |
| C. albicans ATCC # 10231 | 48 hrs | 4.25 | — | — | — |
| | | — | 30 | — | — |
| | | 4.25 | 1.86 | 1.06 | 1:0.4376 |
| | | 4.25 | 0.94 | 1.03 | 1:0.2212 |
| | 72 hrs | 5.25 | — | — | — |
| | | — | 60 | — | — |
| | | 1.1 | 30 | 0.71 | 1.27.2727 |
| | | 2 | 30 | 0.88 | 1:15.0000 |
| | | 3 | 30 | 1.07 | 1:10.0000 |
| | | 4.25 | 15 | 1.06 | 1:3.5294 |
| | | 4.25 | 7.5 | 0.93 | 1:1.7647 |
| | | 5.25 | 3.75 | 1.06 | 1:0.7143 |
| | | 4.25 | 1.86 | 0.84 | 1:0.4376 |
| | | 5.25 | 1.86 | 1.03 | 1:0.3543 |
| | | 4.25 | 0.94 | 0.83 | 1:0.2212 |
| | | 5.25 | 0.94 | 1.02 | 1:0.1790 |
| Ps. aeruginosa ATCC # 9027 | 48 hrs | 212.5 | — | — | — |
| | | — | 125 | — | — |
| | | 21.25 | 75 | 0.70 | 1:3.5294 |
| | | 26.25 | 75 | 0.72 | 1:2.8571 |
| | | 43.75 | 75 | 0.81 | 1:1.7143 |
| | | 55 | 75 | 0.86 | 1:1.3636 |
| | | 100 | 75 | 1.07 | 1:0.7500 |
| | | 150 | 37.5 | 1.01 | 1:0.2500 |
| | | 150 | 18.75 | 0.86 | 1:0.1250 |
| | | 212.5 | 18.75 | 1.15 | 1:0.0882 |
| | | 150 | 9.4 | 0.78 | 1:0.0627 |

TABLE 10-continued

| Test Organisms | Contact Time | Ca | Cb | S.I. | Ca:Cb |
|---|---|---|---|---|---|
| | | 212.5 | 9.4 | 1.08 | 1:0.0442 |
| | | 212.5 | 4.6 | 1.04 | 1:0.0216 |
| S. aureus ATCC # 6538 | 24 hrs | 26.25 | — | — | — |
| | | — | 15 | — | — |
| | | 26.25 | 0.94 | 1.06 | 1:0.0358 |

Ca: ppm AI of TCMTB (2-(thiocyanomethylthio) benzothiazole)
Cb: ppm AI of MBIT(N-methyl-1,2-benzisothiazolin-3-one)
Ratio: Ca:Cb

The invention claimed is:

1. A microbicidal composition comprising:
(a) N-methyl-1,2-benzisothiazolin-3-one; and
(b) at least one microbicide selected from the group consisting of hexahydro-1,3,5-tris(2-hydroxyethyl)-s-triazine; 4,4-dimethyloxazolidine; sodium hydroxymethylglycinate; myristamidopropyl PG-dimonium chloride phosphate; octanoic acid; 2-ethylhexyl glycerin; glyceryl monocaprylate; glyceryl monocaprate; 7α-ethyldihydro-1H,3H,5H-oxazolo (3,4-C) oxazole; and 2-(thiocyanomethylthio)benzothiazole.

2. The microbicidal composition of claim 1 in which said at least one microbicide is hexahydro-1,3,5-tris(2-hydroxyethyl)-s-triazine, and a ratio of hexahydro-1,3,5-tris(2-hydroxyethyl)-s-triazine to N-methyl-1,2-benzisothiazolin-3-one is from 1:0.0014 to 1:150.

3. The microbicidal composition of claim 1 in which said at least one microbicide is 4,4-dimethyloxazolidine, and a ratio of 4,4-dimethyloxazolidine to N-methyl-1,2-benzisothiazolin-3-one is from 1:0.0011 to 1:3.5.

4. The microbicidal composition of claim 1 in which said at least one microbicide is sodium hydroxymethylglycinate, and a ratio of sodium hydroxymethylglycinate to N-methyl-1,2-benzisothiazolin-3-one is from 1:0.0005 to 1:2.3.

5. The microbicidal composition of claim 1 in which said at least one microbicide is myristamidopropyl PG-dimonium chloride phosphate, and a ratio of myristamidopropyl PG-dimonium chloride phosphate to N-methyl-1,2-benzisothiazolin-3-one is from 1:0.0011 to 1:150.

6. The microbicidal composition of claim 1 in which said at least one microbicide is octanoic acid, and a ratio of octanoic acid to N-methyl-1,2-benzisothiazolin-3-one is from 1:0.0046 to 1:0.68.

7. The microbicidal composition of claim 1 in which said at least one microbicide is 2-ethylhexyl glycerin, and a ratio of 2-ethylhexyl glycerin to N-methyl-1,2-benzisothiazolin-3-one is from 1:0.017 to 1:2.3.

8. The microbicidal composition of claim 1 in which said at least one microbicide is glyceryl monocaprylate, and a ratio of glyceryl monocaprylate to N-methyl-1,2-benzisothiazolin-3-one is from 1:0.0004 to 1:75.

9. The microbicidal composition of claim 1 in which said at least one microbicide is glyceryl monocaprate, and a ratio of glyceryl monocaprate to N-methyl-1,2-benzisothiazolin-3-one is from 1:0.0031 to 1:8.8.

10. The microbicidal composition of claim 1 in which said at least one microbicide is 7α-ethyldihydro-1H,3H,5H-oxazolo (3,4-C) oxazole, and a ratio of 7α-ethyldihydro-1H,3H,5H-oxazolo (3,4-C) oxazole to N-methyl-1,2-benzisothiazolin-3-one is from 1:0.0003 to 1:7.1.

11. The microbicidal composition of claim 1 in which said at least one microbicide is 2-(thiocyanomethylthio)benzothiazole, and a ratio of 2-(thiocyanomethylthio)benzothiazole to N-methyl-1,2-benzisothiazolin-3-one is from 1:0.063 to 1:143.

* * * * *